United States Patent
Neel et al.

(10) Patent No.: US 8,696,597 B2
(45) Date of Patent: Apr. 15, 2014

(54) DIAGNOSTIC METER

(75) Inventors: Gary T. Neel, Weston, FL (US); Brent E. Modzelewski, Boca Raton, FL (US); George R. Rounds, Coconut Creek, FL (US); Carlos Oti, Plantation, FL (US); Allan Javier Caban, Lakeworth, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 1536 days.

(21) Appl. No.: 11/395,266

(22) Filed: Apr. 3, 2006

(65) Prior Publication Data

US 2007/0233395 A1 Oct. 4, 2007

(51) Int. Cl.
*A61B 5/00* (2006.01)

(52) U.S. Cl.
USPC .......................................... 600/584; 600/300

(58) Field of Classification Search
USPC .......... 128/903, 904; 600/300, 345, 347, 583, 600/584
See application file for complete search history.

(56) References Cited

U.S. PATENT DOCUMENTS

| | | | |
|---|---|---|---|
| 5,728,074 A * | 3/1998 | Castellano et al. ............ | 604/207 |
| 7,344,500 B2 | 3/2008 | Talbot et al. | |
| 2002/0002326 A1 * | 1/2002 | Causey et al. ................. | 600/300 |
| 2003/0005336 A1 * | 1/2003 | Poo et al. ....................... | 713/202 |
| 2004/0039255 A1 * | 2/2004 | Simonsen et al. ............. | 600/300 |
| 2004/0225832 A1 * | 11/2004 | Huang ........................... | 711/105 |
| 2004/0249999 A1 | 12/2004 | Connolly et al. | |
| 2004/0260204 A1 * | 12/2004 | Boecker et al. ................ | 600/584 |
| 2004/0260854 A1 | 12/2004 | Schade | |
| 2005/0096518 A1 | 5/2005 | Chang | |
| 2005/0096565 A1 * | 5/2005 | Chang ............................ | 600/584 |
| 2005/0168747 A1 | 8/2005 | Fox | |
| 2005/0214929 A1 * | 9/2005 | Seher et al. ................. | 435/287.2 |
| 2006/0009684 A1 | 1/2006 | Kim | |
| 2006/0044871 A1 | 3/2006 | Tanikawa et al. | |
| 2007/0123782 A1 * | 5/2007 | Connolly et al. ............. | 600/483 |
| 2007/0208233 A1 * | 9/2007 | Kovacs ......................... | 600/300 |
| 2007/0233395 A1 | 10/2007 | Neel et al. | |
| 2007/0239990 A1 * | 10/2007 | Fruhauf et al. ................ | 713/185 |
| 2008/0045819 A1 | 2/2008 | Emoto et al. | |
| 2010/0069730 A1 * | 3/2010 | Bergstrom et al. ........... | 600/365 |

FOREIGN PATENT DOCUMENTS

| | | |
|---|---|---|
| JP | 2000-504597 A | 4/2000 |
| JP | 2001-258867 A | 9/2001 |
| JP | 2002-521692 A | 7/2002 |
| JP | 2003-215122 A | 7/2003 |
| JP | 2003-288660 A | 10/2003 |
| JP | 2005-525161 A | 8/2005 |

(Continued)

OTHER PUBLICATIONS

International Search Report received from the European Patent Office, dated Oct. 22, 2007.

(Continued)

*Primary Examiner* — Max Hindenburg
*Assistant Examiner* — Jonathan M Foreman
(74) *Attorney, Agent, or Firm* — Finnegan, Henderson, Farabow, Garrett & Dunner

(57) ABSTRACT

A system for diagnostic testing, including a meter assembly that communicates with a partner device, such as a PC. The device can be made compact, convenient to carry, and easily connectable to a variety of electronics devices.

21 Claims, 12 Drawing Sheets

(56) References Cited

FOREIGN PATENT DOCUMENTS

| JP | 2006-066009 A | 3/2006 |
|----|---|---|
| TW | 562480 | 11/2003 |
| TW | 200606647 A | 2/2006 |
| WO | WO 97/28736 | 8/1997 |
| WO | WO 00/07013 A2 | 2/2000 |
| WO | WO 03/094713 A1 | 11/2003 |
| WO | WO 2004/090503 A2 | 10/2004 |
| WO | WO 2005/011488 A | 2/2005 |
| WO | WO 2006/009199 A1 | 1/2006 |

OTHER PUBLICATIONS

AU Examination Report dated Mar. 27, 2012, issued in Australian Patent Application No. 2007234940.

EP Examination Reported dated Sep. 8, 2009, issued in European Patent Application No. 07759939.7.

JP Office Action dated Oct. 14, 2011, issued in Japanese Patent Application No. 2009-504403.

JP Office Action dated Oct. 10, 2012, issued in Japanese Patent Application No. 2009-504403.

MX Office Action dated Jan. 25, 2012, issued in Mexican Patent Application No. MX/a/2008/012709.

MX Office Action dated Jun. 22, 2012, issued in Mexican Patent Application No. MX/a/2008/012709.

PCT Written Opinion of the International Searching Authority, issued in International Application No. PCT/US2007/065763 dated Oct. 22, 2007.

PCT Notification of Transmittal of the International Search Report and the Written Opinion of the International Searching Authority, issued in International Application No. PCT/US2007/065763 dated Oct. 22, 2007.

PCT International Preliminary Report on Patentability, issued in International Application No. PCT/US2007/065763 dated Oct. 8, 2008.

Taiwanese Search Report issued in Taiwanese Patent Application No. 96111047 dated Nov. 2, 2012.

\* cited by examiner

FIG. 3A
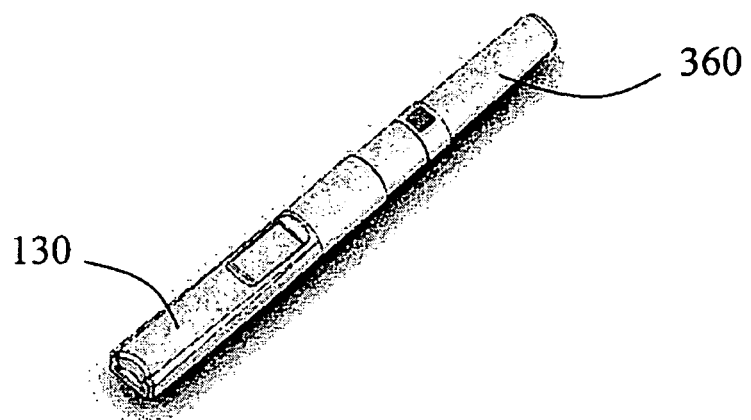
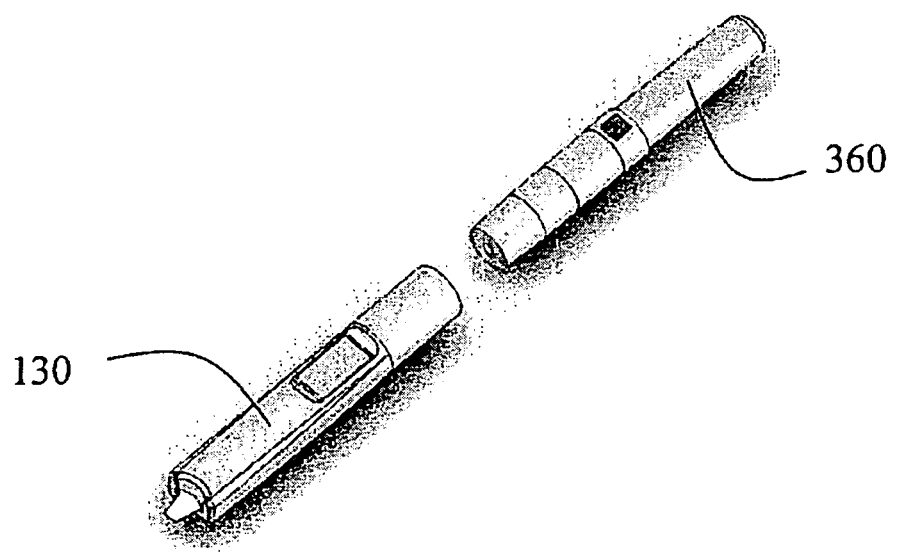
FIG. 3B

DIAGNOSTIC METER

TECHNICAL FIELD

The present invention relates to the field of diagnostic testing and, more particularly, to diagnostic testing systems using electronic meters and digital communication.

BACKGROUND

Diagnostic testing systems are commonly used to perform various assays on various types of samples. The diagnostic test may be a qualitative or quantitative test to determine the presence, concentration or amount of one or more analytes in a sample. The analyte may be a medically significant analyte—e.g., glucose, ketones, cholesterol, triglycerides, human choriogonadotropin (HCG), hemoglobin A1C, fructosamine, carbohydrates, tumor markers, lead, anti-epilepsy drugs, bilirubin, liver function markers, toxins or their metabolites, controlled substances, blood coagulation factors (PT, ATPP), etc.—contained in a biological sample—e.g., blood, urine, tissue, saliva, etc. However the diagnostic test is not limited to the medical field. Diagnostic test meters can also be used to monitor analytes or chemical parameters in non-medical samples such as water, food products, soil, sewage, sand, air, or any other suitable sample.

Diagnostic testing systems can include test media (e.g., a test strip, tab, disc, etc.) configured to react to a specific analyte or analytes in a sample, and a separate electronic device configured to interface with the test media, conduct the diagnostic test, and indicate the results of the diagnostic test to the user.

To conduct a diagnostic test using most prior art systems, a user must first obtain test media, e.g., a test strip from a container, and then obtain a test sample to introduce to the test media. Acquiring a sample, such as blood, may require the use of a sampling device (e.g., a lancet). According to the operation of the prior art system, the user applies the sample to the test media either before or after inserting the test media into the meter interface. The meter then performs a diagnostic test on the sample and indicates the test result to the user, e.g., using a visual display.

Most diagnostic meters have an onboard memory for storing results over a period of time so that a user can record test results and, with the help of a health care professional, evaluate trends in the test data. Some systems known in the art also allow uploading test result data to a personal computer using an appropriate data cable. The user may then use software pre-installed on the personal computer to display and analyze the data, or to transmit the test results to a physician so that an assessment of the patient's condition can be made. The pre-installed software includes any drivers necessary to allow the diagnostic meter, which is a specialized device, to interface with the PC. Because it is usually inconvenient for the user to carry a data cable, along with the diagnostic meter hardware while away from home, the meter's user will usually use the meter's onboard memory to store test results until the user can upload the results to a PC. Since it may be somewhat inconvenient and tedious to connect the meter to the computer via the data cable, a period of days or even weeks can elapse before data is transferred to the computer. This delay can translate to missed opportunities to diagnose important trends in the data.

An additional limitation of many prior art diagnostic meters is that they are sometimes bulky because the housings contain a large visual display and electronics to support various functions. Some meters also employ test media cartridges (e.g., a disk) that add additional size and weight to the meter. In addition, the user of a blood testing diagnostic system must manage and carry not only the meter, but also a supply of test media and a lancet set. The lancet set includes both a lancing device body and a supply of lancet points, where a new lancet point is used for each diagnostic test. These three components must be manipulated in a certain order and require a substantial amount of attention and technique to conduct a successful test. Not only are the steps cumbersome to some users, but there exists the possibility that the test media container, sampling device and meter could be separated from each other, so that the user may find themselves without one or more of the components necessary to conduct the diagnostic test.

A well-known limitation to users of diagnostic testing systems is the need for the user to "code" the meter. Test media from different manufacturers or media from different manufacturing lots may respond differently to the presence or concentration of analyte in a sample. In order to obtain more accurate results, the electronic meter may be calibrated with one or more calibration parameters that correlate the signal response from a particular brand or lot of test media to a standardized reference. Without such calibration, the results reported by the meter may not accurately represent the amount of analyte in the sample. In some prior art systems, the user may be required, in addition to the above steps, to manually enter an appropriate calibration code number, from which the meter can access the appropriate calibration information stored in the meter's memory. In another approach, each test media container may be provided with an associated code chip, e.g. a ROM, on which the calibration data is stored electronically. The user may provide the calibration data to the meter by inserting the code chip into a corresponding port on the meter.

These prior art coding methods can be inconvenient or difficult for the user. For example, elderly, blind, or infirm users may have difficulty downloading calibration data. Additionally, inserting code chips, which must be physically aligned properly in order to achieve a data connection with the meter, can also be difficult for some users. Moreover, code chips can be misplaced or lost, leading to the inability to use corresponding test media, or using the test media with an unmatched coding device. Further, users may forget to calibrate the meter for use with a new brand or lot of test media. Consequently, the user may use incorrect calibration parameters or codes resulting in inaccurate test results. Where the test is a self-test of blood glucose level, an erroneous result could lead the user to act, or fail to act, in a manner detrimental to his or her health.

Accordingly, there is a need for an improved integrated diagnostic testing system that avoids the disadvantages of the prior art, is convenient to carry, and minimizes the chances of improper calibration.

SUMMARY OF AN ILLUSTRATIVE EMBODIMENT

The illustrative embodiments described herein meet these and other needs by providing an integrated diagnostic testing system including a remote diagnostic meter for performing a diagnostic test on a sample applied to test media, the meter including a housing, a mass storage device, and a data interface device, wherein the housing contains a test media interface. The diagnostic meter may optionally include a display for displaying the test results.

According to the illustrative embodiments, in order to provide a meter that is small, portable and convenient to carry, the meter may not include a display for displaying the test results.

The meter can be wirelessly connected to a partner device, such as a MP3 player, cell phone, digital camera, personal digital assistant, or other similar wireless information device, in order to display the test results on the partner device's high quality screen.

The illustrative embodiments further provide mechanisms for coupling a remote diagnostic meter and a computer for communication, without the requirement that the user perform any special set-up steps. Data can be directly downloaded from the remote meter and stored onto a personal computer or stored in the meter, for example, in flash memory of a USB data connector. The illustrative embodiments described herein provide a USB data connector of the diagnostic meter wirelessly connected to the computer. The wireless communications devices may be RF, IR, BlueTooth®, Near Field Communication (NFC), or other similar devices consistent with the principles of the present invention.

Illustrative embodiments of the present invention alternatively provide a remote meter pre-paired with a transceiver dock or a cradle, in the event a partner device is not equipped with wireless technology. The dock can be affixed to a partner device, such as a MP3 player, and communicate with the partner device via a hardwired connection. Wired communications between the dock and the partner device, in conjunction with wireless communications between the dock and the remote meter, provide a means for a non-wireless partner device to benefit from the same wireless functionality as if the partner device was, in fact, wireless itself.

The illustrative embodiments further provide a diagnostic meter calibrated for use with a particular lot of test media by coding with appropriate calibration parameters. The meter may be configured to read a calibration code on the diagnostic test strip. Alternatively, the meter may only be provided with strips corresponding to a preprogrammed set of calibration data for use with the meter.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention, and together with the description, serve to explain the principles of the invention.

FIGS. 3A and 3B are perspective views of a second illustrative embodiment of an integrated remote diagnostic meter assembly consistent with the present invention.

DESCRIPTION OF ILLUSTRATIVE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

1. Exemplary Systems

Figure 1:
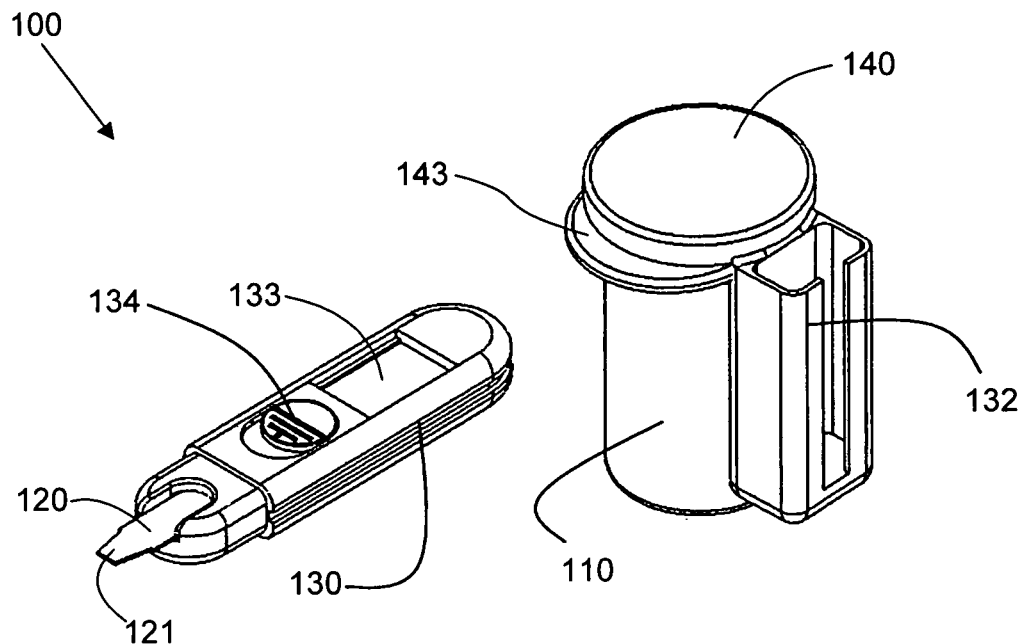
FIG. 1 is a perspective view of a first illustrative embodiment of an integrated remote diagnostic meter assembly consistent with the present invention.

FIG. 1 is an integrated system 100 for conducting a diagnostic test in accordance with an exemplary embodiment of the present invention. Exemplary integrated system 100 can include a container 110 with a closure 140 for containing test media, such as test strips 120, and a stand-alone remote meter 130 for performing a diagnostic test using the test strips 120 contained in container 110, including a display 133 for displaying the test results.

Alternatively, remote meter 130 may be provided without a display 133 (not shown) in order to keep manufacturing costs at a minimum and the meter device small and compact. Meter 130 can be wirelessly connected to a partner device, such a MP3 player, cell phone, digital camera, personal digital assistant, or other similar wireless information device, in order to display the test results on the partner device's high quality screen. Those of skill in the art will recognize that other technology, similar to wireless technology, is equally applicable to connect meter 130 and the partner device. By off-loading the bulk of the diagnostic system, i.e. display, result memory, user interface, etc., to a multi-purpose partner device with these built-in capabilities, the meter 130 can be reduced in size to only include the essentials, i.e. a strip connector, data acquisition system, and wireless communication module. Reduced size and wireless connectivity makes the remote meter 130 highly portable, while providing a large remote display and remote data management.

In this exemplary embodiment, container 110 and closure 140 are formed of polypropylene using an injection molding process, but other materials known in the art can be used. Container 110 and closure 140 can be configured to prevent the infiltration of light, liquid, vapor, and/or air into the container 110 to prevent contamination or degradation of the test media. Where the test media may be toxic or may present a choking hazard to children, closure 140 may optionally be configured to be locked or child-resistant, as is known in the art. Illustratively, the container 110 is shown as a right circular cylinder, however, the container 110 and its opening may be made in a number of other shapes. The container 110 can also be customized with graphical designs appealing to individual users, or the corporate logos of co-branding partners, etc.

Figure 12:
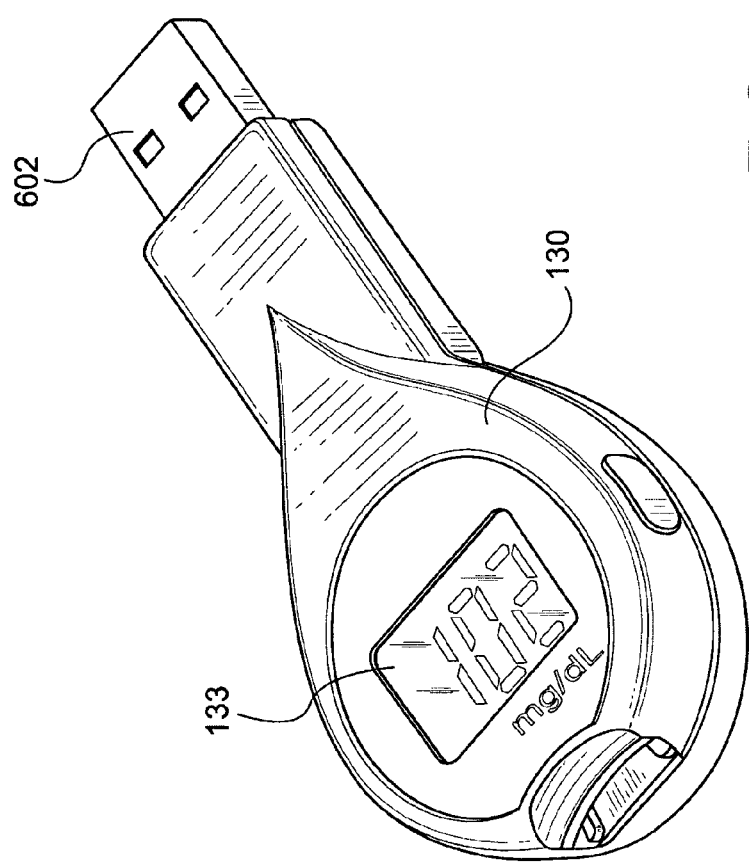
FIG. 12 is a perspective view of an illustrative integrated remote diagnostic meter assembly shaped to close an opening of a container.

Alternatively, as illustrated in FIG. 12, remote meter 130 may have an exterior shape similar to that of the container 110 so that the integrated system 100 can attach to and engage with an opening of the container 110 in order to selectively close the opening thereof. The remote meter 130 further includes a data connector 602 adapted to interface with a computer 112, as further described below. As would be apparent to one of ordinary skill in the art, and as discussed herein, attach to may be used to signify affiliated with, associated with, affixed with/to, connected with/to, coupled with/to, fastened with/to, fixed with/to, secured with/to, etc. It will also be understood that the container 110 and the meter 130 may be configured in different shapes without departing from the scope of the present invention. Exemplary meter housing and container embodiments are described in commonly-assigned co-pending U.S. patent application Ser. No. 10/857,917, filed Jun. 2, 2004, and U.S. patent application Ser. No. 11/254,881, filed Oct. 21, 2005, both of which are incorporated by reference herein in their entirety.

Additionally, as illustrated in FIG. 1, closure 140 is provided with a protrusion 143 which extends beyond the side of container 110, to sufficiently aid the user in opening and closing the container 110, e.g., by pushing upward with the thumb against the protrusion 143. The container 110 and closure 140 may be integrally connected by a hinge, e.g., as shown in U.S. Pat. No. 5,723,085, entitled "PROCESS AND APPARATUS FOR MAKING A LEAK PROOF CAP AND BODY ASSEMBLY," which is incorporated by reference herein in its entirety. Additionally, container 110 and closure 140 may be integrally connected by a lanyard or other flexible connector, such as a flexible plastic band or wire, etc. (not shown). Alternatively, one end of the connector may be connected to a ring (not shown) that is sized to fit over container 110. The ring may be configured to loosely and frictionally engage container 110. As another alternative, the ring may be affixed to the container 110, e.g., by welding, gluing, etc.

For blood glucose testing, meter 130 may employ any variety of techniques. Illustratively, the diagnostic test employs an electrochemical technique (e.g., coulometry, amperometry, potentiometry, etc.). Exemplary electrochemical systems are described in prior U.S. Pat. No. 6,743,635, issued Jun. 1, 2004, and U.S. Pat. No. 6,946,299, issued Sep. 20, 2005, both entitled "SYSTEM AND METHOD FOR BLOOD GLUCOSE TESTING" and commonly assigned with the instant application, both of which are incorporated by reference herein in their entirety. Alternatively, meter 130 may employ a photometric technique (e.g., reflection, transmission, scattering, absorption, fluorescence, electro-chemiluminescence, etc.) to determine the amount of glucose in the sample. Exemplary photometric systems are described in U.S. Pat. Nos. 6,201,607, 6,284,550 and 6,541,266, each commonly-assigned with the instant application, which are incorporated by reference herein in their entirety. Electrochemical systems are currently popular because, among other reasons, they require a smaller blood sample (on the order of 1 μL or less) than the photometric techniques (on the order of 1 μL or greater), and electrochemical meters typically require less power and are smaller than their photometric counterparts.

Integrated system 100 will be illustrated with reference to a diagnostic test to determine the concentration of blood glucose using an electrochemical technique, with the understanding that the principles of the present invention are equally applicable to other types of diagnostic tests and techniques, such as those mentioned above. Further, although the present invention has been illustrated as utilizing test media in the form of test strips 120, exemplary embodiments of the present invention are not limited to a particular type of media, and those of skill in the art will recognize that the principles of the present invention are equally applicable to diagnostic testing systems which employ test media in other forms, e.g., tabs, discs, etc.

As depicted in FIG. 1, meter 130 may be attached to test strip container 110 via a holster-type receptacle 132 formed on the side of the test strip container 110. Additionally, a strip ejector mechanism 134 can be provided on the meter 130 to dispose of the strip 120 without touching.

Figure 2:
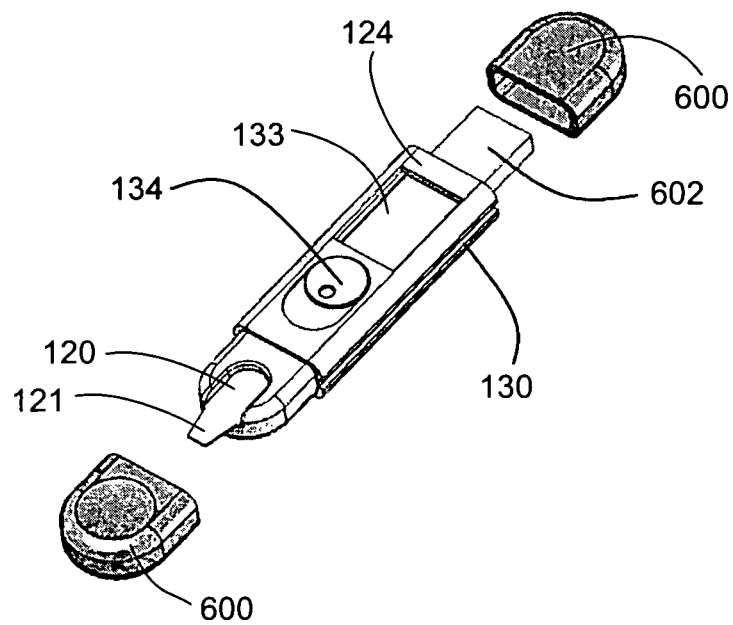
FIG. 2 illustrates a perspective view of a remote diagnostic meter with an integrated data connector consistent with the present invention.
Figure 4:
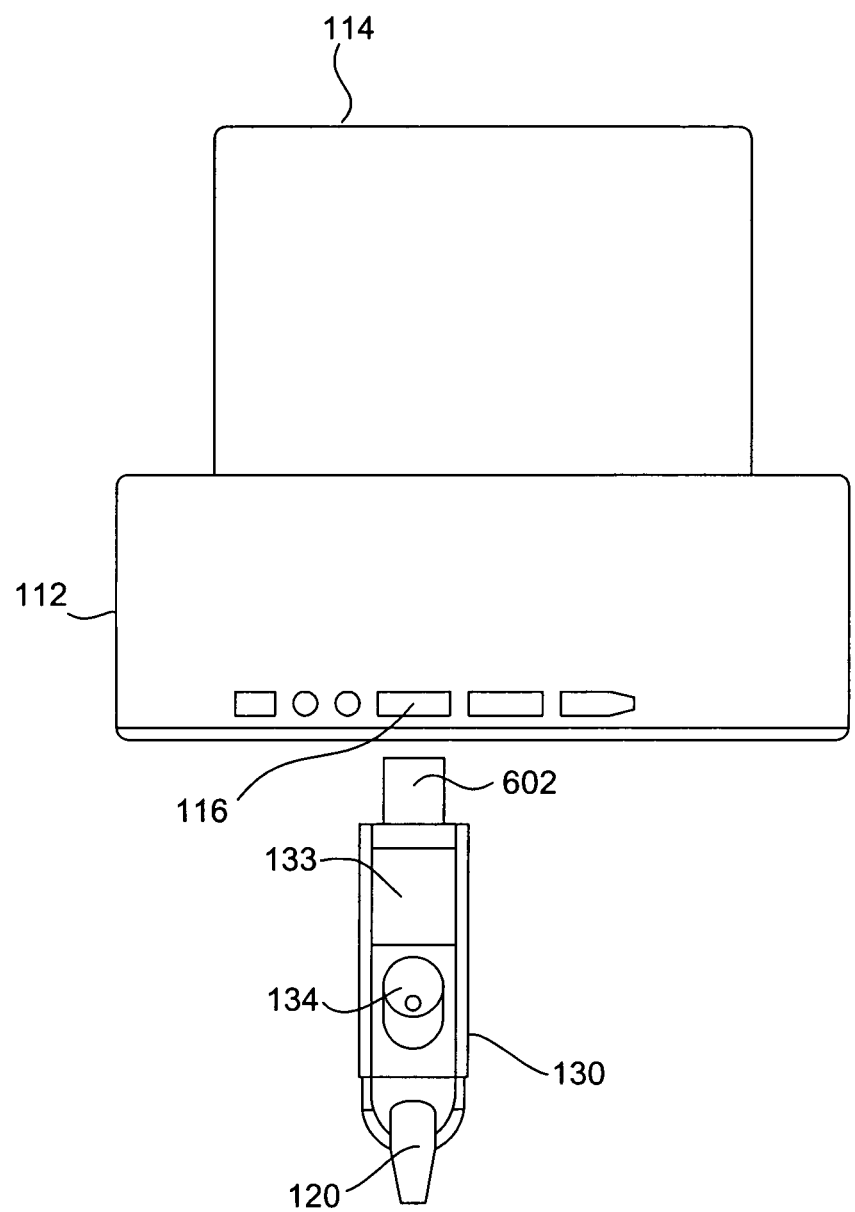
FIG. 4 is a perspective view of a meter interfacing with a computer.

As illustrated in FIG. 2, integrated meter 130 includes a data connector 602 adapted to interface with a computer, as further illustrated in FIG. 4. Protective covers 600 may be attached to the ends of meter 130 to protect the sample chamber 121 and USB data connector 602 from contamination, static electricity and damage. The covers 600 can vary in size, shape, color or texture to provide for tactile and visual discrimination.

Alternative embodiments provide a meter 130 attached to a lancing device 360 that can be used together or separately as illustrated in FIGS. 3A and 3B. The integrated meter-lancing device can also be attached to a vial, as shown in FIG. 1, by a holster or other known means or attachment. Further details of exemplary lancing device 360 are shown in prior application Ser. No. 10/757,776, entitled "LANCING DEVICE," filed Jan. 15, 2004, commonly-assigned with the instant application, which is incorporated by reference herein in its entirety. However, the present invention is not limited to any particular sampling device, and one of skill in the art will recognize that other sampling devices can be incorporated in a manner similar to the exemplary lancing device described above.

2. Interface of Meter with a Partner Device

Plug and Play in Windows® based computers, as well as analogous Apple Mac protocols, allow a user to connect a hardware device and have the operating system configure and start the hardware. However, computer hardware, device drivers, and the operating system must all be in sync to allow installation without user intervention. For example, although Windows® provides plug-and-play functionality, if no device driver compatible with detected new hardware is available, the operating system cannot automatically configure and start the device. For this reason, prior art diagnostic meters require the user to first download and install device drivers before connecting the meter to the computer.

After a computer detects the connection of a new device, the operating system checks which hardware resources the device needs (such as interrupts, memory ranges, I/O ranges, and DMA channels) and assigns those resources. These requirements are derived from a hardware identification number provided by the device. The operating system then checks the availability of a driver that matches the hardware identification number of the device. The operating system can also choose among several drivers, should more than one be identified.

If the device is not automatically installed by the operating system, the procedure becomes increasingly complicated as the operating system will request from the user information about the device and where to find drivers. For non-standard devices, such as diagnostics meters, specialized drivers are required. Also, for networked computers under administrative control, such as those most frequently encountered in the workplace and those generally available for public access, restricted privileges are required for a user to install or configure a specialized, non-standard device.

Figure 5:
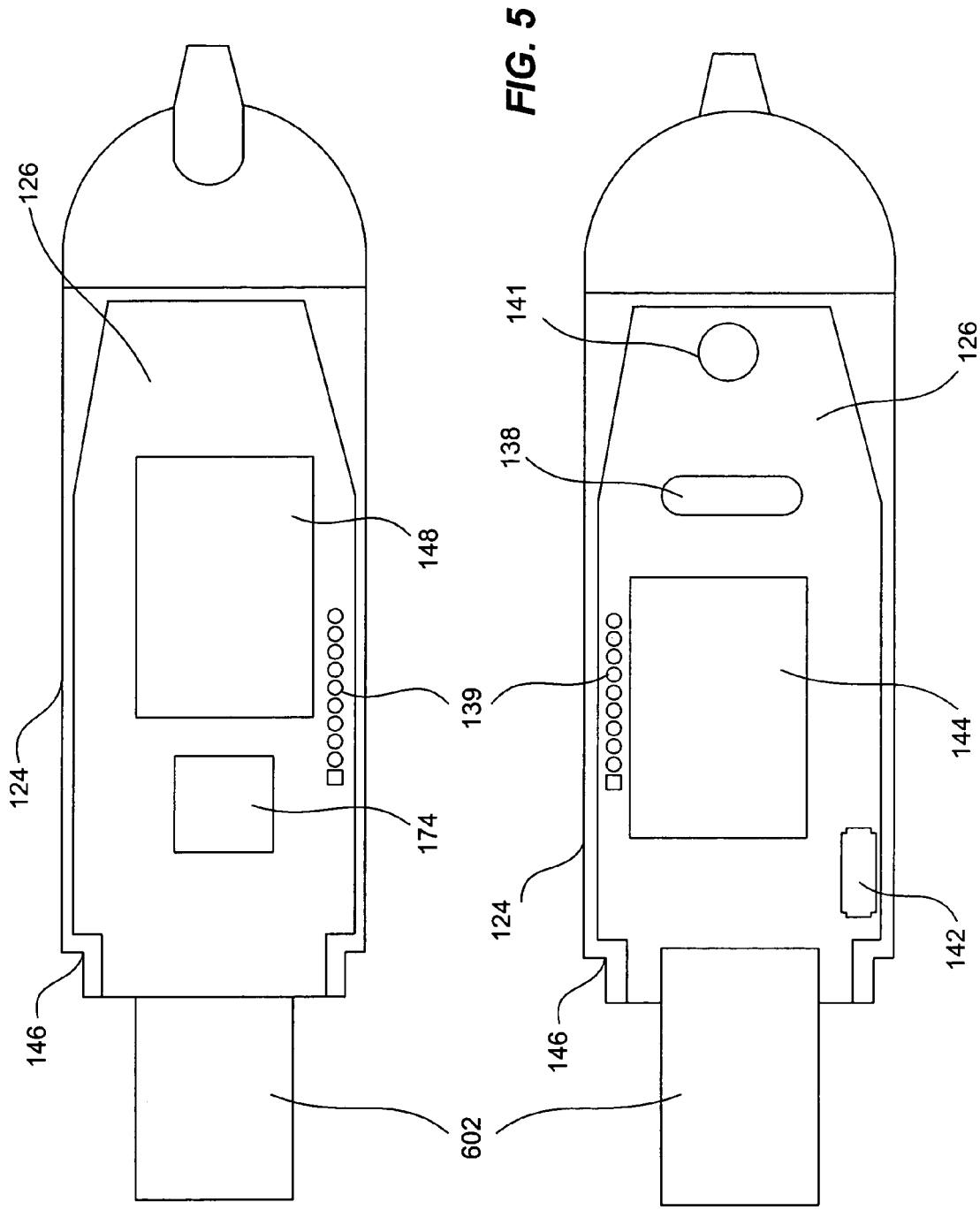
FIG. 5 illustrates a perspective view of a data connector portion of a meter consistent with the invention.
Figure 6:
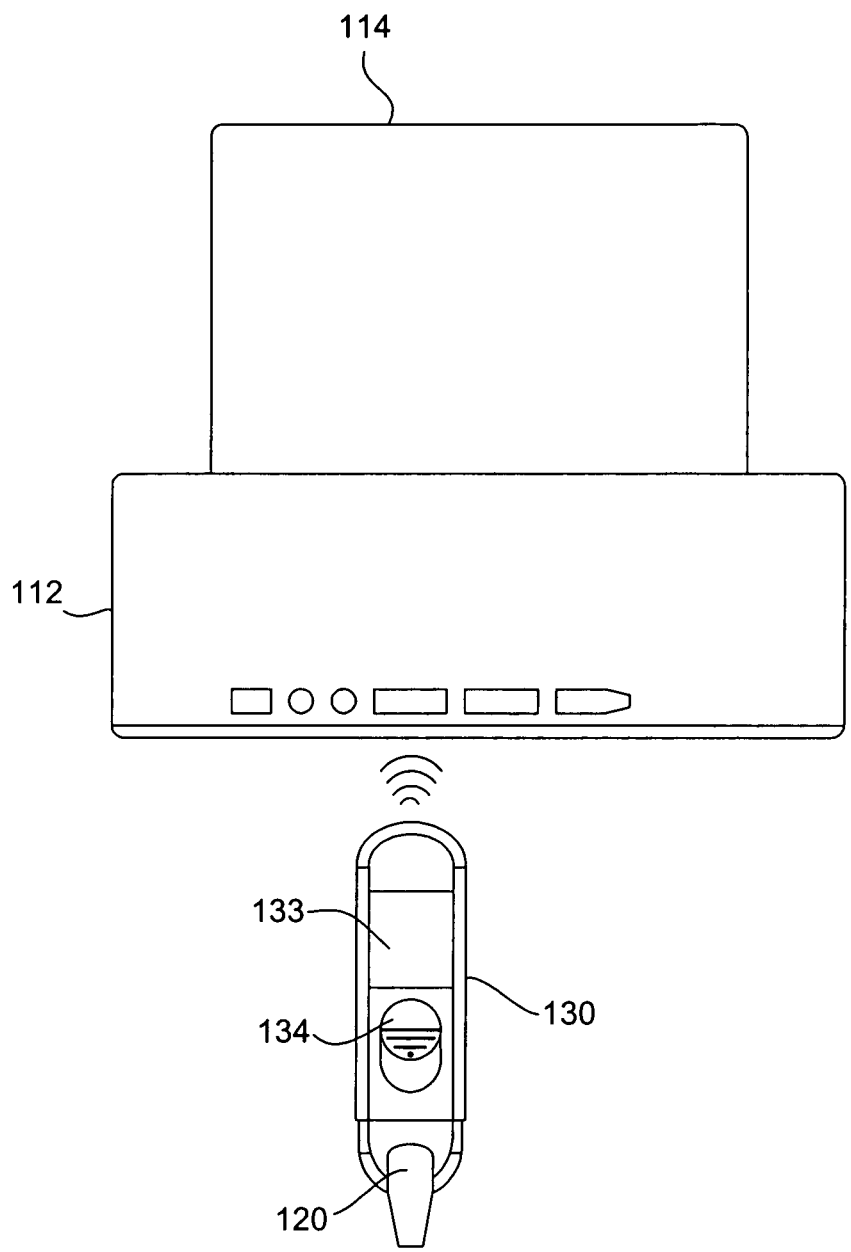
FIG. 6 is a perspective view of an illustrative integrated remote diagnostic meter assembly wirelessly communicating with a computer.

The present invention provides mechanisms for coupling a remote diagnostic meter 130 and a computer 112 for communication, as shown in FIGS. 4 and 6, without the requirement that the user perform any special set-up steps. Data can be directly downloaded from the remote meter 130 and stored onto a personal computer 112 or stored in the meter 130, for example, in a flash memory 148 of a USB data connector 602, as illustrated in FIG. 5.

FIG. 4 depicts an exemplary diagnostic testing meter 130 configured to interface with test media 120 to measure glucose levels in a blood sample and transfer the test results to a personal computer 112 via a USB data connector 602. Computer 112 processes and stores data received from the meter via USB port 116, and further comprises a monitor 114 or any other output device for displaying data from the meter 130. The monitor 114 can display basic test results, but additionally, can display date, time, trend analysis, etc. Alternatively or in addition, there are several types of data connectors that are applicable to the method and apparatus of the present invention. In addition to USB connectors, there are Ethernet, Fire Wire, SCSI, modem, wireless, video, printer, serial data couplings, and several more. However, it will be understood that the present invention is not limited to any particular type of data connector and that other data connectors may be employed consistent with the principles of the present invention.

FIG. 5 illustrates an exemplary USB interface connected to data connector 602. Inside meter housing 124 is a small, highly cost-engineered, printed circuit board 126. Mounted on this board 126 can be various components including simple power circuitry and surface-mounted integrated circuits (ICs). The printed circuit board 126 can include a mass storage controller 174, a NAND flash memory chip 148, and a crystal oscillator 138, which produces the USB data connector's 602 main clock signal and controls the data output through a phase-locked loop. Mass storage controller 174 implements the USB host controller and provides seamless interface to block-oriented serial flash devices, while hiding the complexities of block-orientation, block erasure, and wear balancing. The controller 174 can further contain a small reduced instruction set computer (RISC) microprocessor (not shown) and a small amount of on-chip read only memory (ROM) and random access memory (RAM) (not shown).

Flash memory chip 148 includes a non-volatile memory, so as to retain the stored data when un-powered. For example, flash memory chip 148 can be an electronically erasable programmable read only memory ("EEPROM") chip. Such EEPROM chips can typically be written to many times (e.g., one million write cycles, or more) so that it does not wear out over the life cycle of usage. In one embodiment, a number of communication protocol drivers are stored in the read only memory of flash memory chip 148. An appropriate driver is chosen from the library of available communication protocol drivers when the USB data connector 602 is inserted into the port 116 of the computer 112. In another embodiment of the present invention, an appropriate communication protocol driver is transferred from the USB data connector 602 of the remote meter 130 and stored in the computer's memory 206.

Board 126 can additionally include jumpers and test pins 139 for testing during the data connector's manufacturing, light emitting diodes (LEDs) 141 that, in use, indicate data transfer or data reads and writes, and a write-protect switch 142 which indicates whether the device is in write-protection mode. As depicted, an unpopulated space 144 provides space to include optional circuitry, such as a second memory chip (not shown). This second space 144 allows the manufacturer to develop only one printed circuit board 126 that can be flexibly used for more than one device. The meter according to this exemplary embodiment can provide flash drive functionality, in addition to serving as a diagnostic meter. Plug and Play functionality is conventionally available for mass storage devices such as flash drives. The presence of a test strip 120 in the meter can be used to signal to the device whether to implement the USB host controller as a flash drive or as a diagnostic meter. Of course, other methods to switch functionality can be employed, such as a switch, the position of the strip ejector 134, etc. When the USB host controller is implemented as a flash drive, meter 130 can transfer the test results to the flash memory chip 148 of the flash drive. A partner device can then process and store the test results or display the data on a monitor by directly accessing the data from the flash memory chip 148 of the flash drive.

While discussed above in relation to a general purpose computer 112, the partner device connectable to the meter can be one or more of several devices, such as MP3 players, cell phones, digital cameras, personal digital assistants, printers, and wireless information devices.

Alternatively, FIG. 6 illustrates the USB data connector 602 wirelessly connected to the computer 112. The wireless communications devices may be RF, IR, BlueTooth®, Near Field Communication (NFC), or other similar devices consistent with the principles of the present invention. The RF device can operate in a range of about 2.4 GHz to about 2.48 GHz and has an output in a range of about −30 to +20 dBm (100 mW). Furthermore, the RF device may be enabled for spread spectrum, frequency hopping, and full-duplex operation. In the frequency hopping operation, the RF device may be enabled for operation up to 1600 hops/sec, where a signal hops among 79 frequencies at 1 MHz intervals. Alternatively, the wireless communications device may be an IR device which can operate on a wavelength in a range of about 850 nm to about 1050 nm. Other and additional protocols can also be implemented, such as ZigBee®, WiFi, 802.11-series wireless, Pre-N, MIMO, etc.

Figure 7:
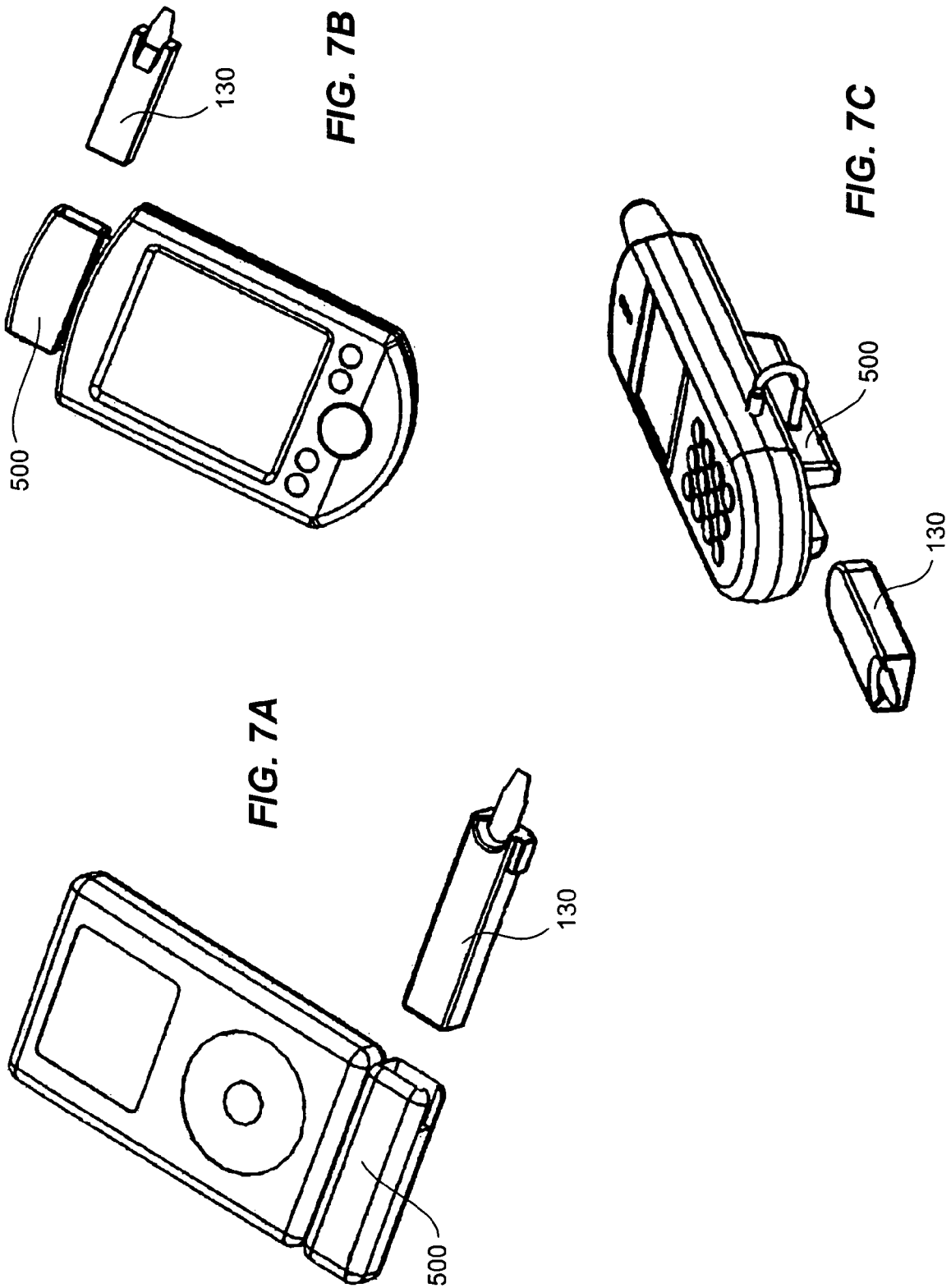
FIGS. 7A, 7B, and 7C are perspective views of a remote diagnostic meter pre-paired with a docking transceiver.

As would be evident to one of ordinary skill in the art, the meter 130 may be configured for both physical and wireless connection. Because not all partner devices, such as a MP3 player, may be equipped with standard RF technology, the remote meter 130 can be pre-paired with a separate transceiver dock 500, as illustrated in FIGS. 7A-7C. The remote meter 130 and dock 500 can communicate wirelessly. The dock 500 is affixed to a partner device and communicates with the partner device via a hardwired connection. Wired communications between the dock 500 and the partner device, in conjunction with the wireless communications between the dock 500 and the remote meter 130, provide a means for a non-wireless partner device to benefit from the same wireless functionality as if the partner device was, in fact, wireless itself.

Figure 13A:
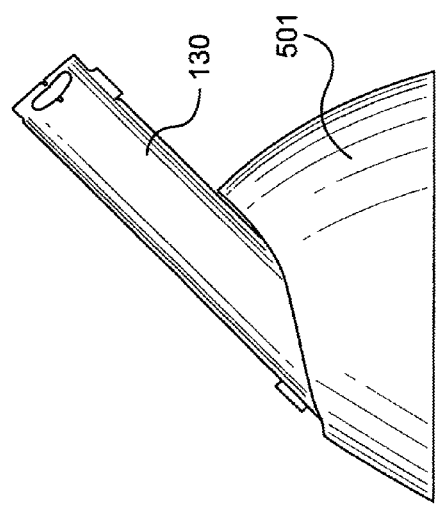
FIGS. 13A and 13B are perspective views of a remote diagnostic meter pre-paired with a cradle.
Figure 13B:
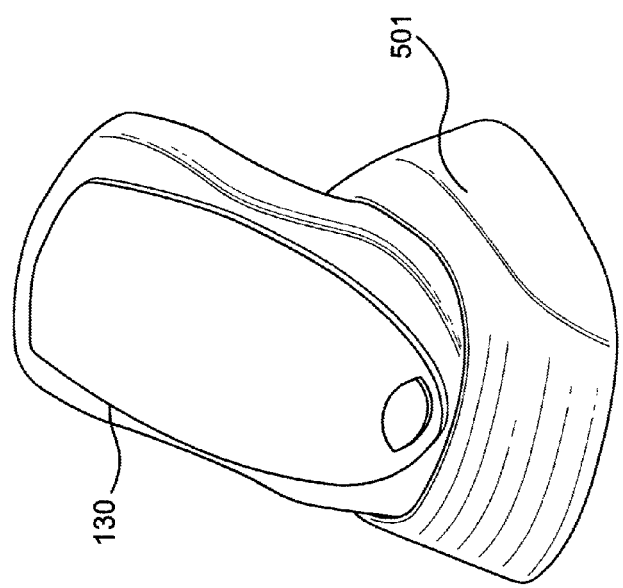

Similarly, a battery-powered BlueTooth® cradle 501, as illustrated in FIGS. 13A and 13B, can be plugged into a 3-wire stereo socket in an end of the remote meter 130. The cradle 501 and the remote meter 130 can communicate wirelessly with a partner device, such as a BlueTooth® compatible cell phone, to send and transmit the test result data. The BlueTooth® cradle 501 serves as a remote communication link between the remote meter 130 and the partner device, such as a cell phone. However, it will be understood that the present invention is not limited to any particular type of cradle and that other cradles may be employed consistent with the principles of the present invention.

One of the many advantages of having a remote meter 130 pre-paired with a dock 500 or a cradle 501 is that it eliminates the step of establishing a pairing relationship between the meter 130 and the partner device. Typically, two wireless devices need to be "introduced" to each other in order to establish a paired relationship. However, pre-paired devices have this relationship built-in during manufacturing. Additionally, the pre-paired docking system provides a highly flexible remote meter 130, wherein a user can choose to use the dock 500 or the cradle 501 with a partner device without built-in wireless technology, or simply use the remote meter 130 without the dock 500 or the cradle 501 when connecting to a device that has built-in wireless technology.

When the meter 130 and the dock 500 or the cradle 501 are used with a non-wireless partner device, the remote meter 130 can perform a diagnostic test while either in or out of the dock 500 or the cradle 501. The dock 500 or the cradle 501 can be used simply as a storage location for the remote meter 130, or alternatively, can be used as a charging facility. Additionally, affixing the dock 500 to a PDA, cell phone, or other similar device, and performing a test while the meter 130 is inserted into the dock 500, allows the entire system to function like a conventional glucose meter.

3. Diagnostic System Functions

Figure 8:
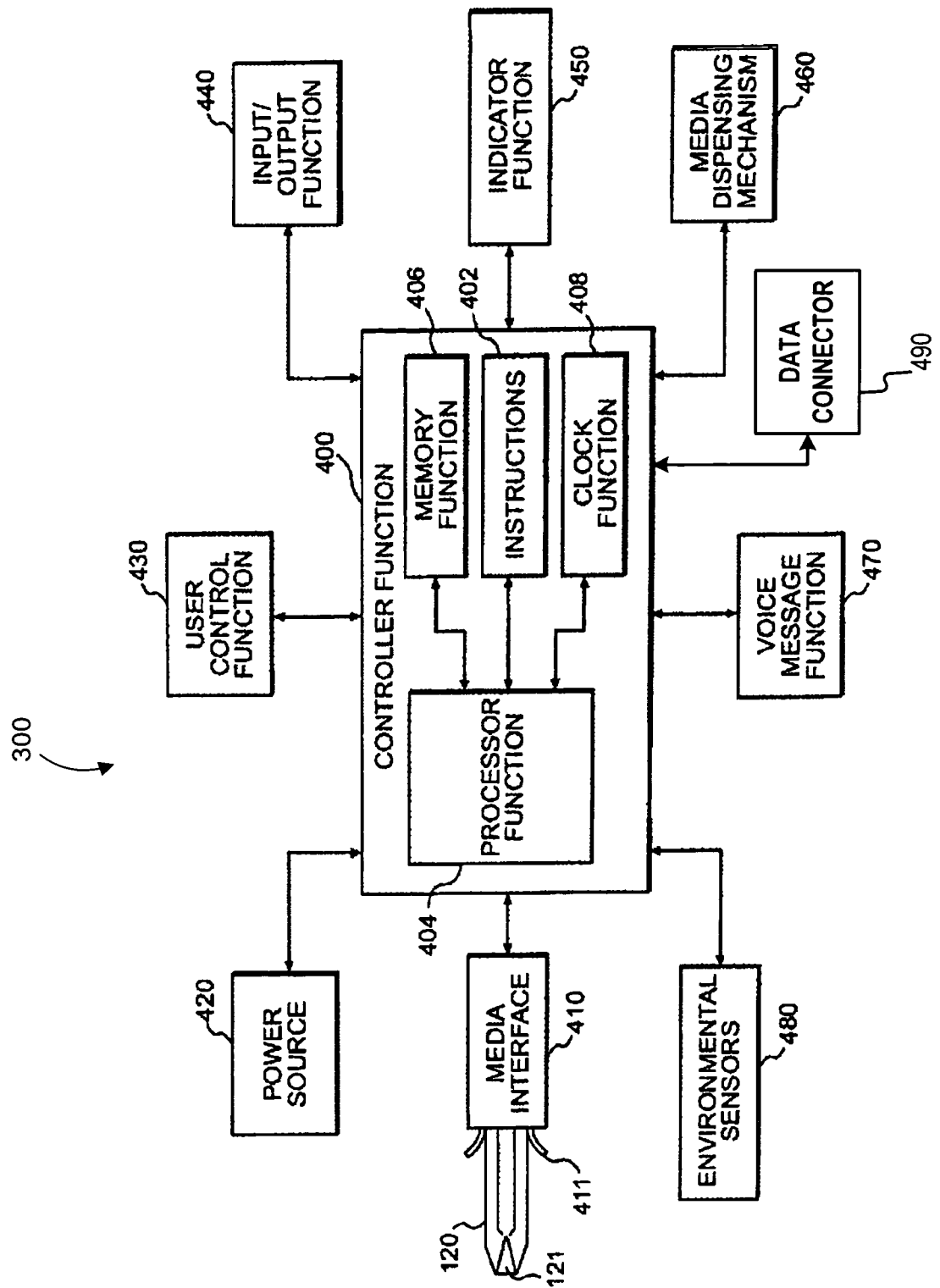
FIG. 8 illustrates an exemplary block diagram of an electronic diagnostic meter consistent with the present invention.

FIG. 8 shows is a block diagram illustrating functional components of exemplary system 300. Diagnostic system 300 may include controller function 400, media interface 410, power source 420, user control function 430, input/output function 440, indicator function 450, media dispensing mechanism 460, voice message function 470, environmental sensors 480, and a data connector 490. In an illustrative embodiment, many of the functional components of the system 300, or portions thereof, are distributed off of the meter 130, and are performed by a partner device, such as a computer. Other partner devices, such as MP3 players, digital cameras, PDA devices, and cell phones, can also be used without departing from the scope of the present invention. Many devices presently available on the market combine the features of one or more of these partner devices. The meter portion of the system, which houses the media interface 410, can communicate with the partner device by physical connection, or wirelessly, as exemplified in FIG. 6 and discussed above.

Controller 400 controls the operation of the functional components of the meter in accordance with its instructions 402, which may be provided as software or firmware. Controller 400 may include microprocessor 404, onboard memory 406, and clock functions 408. In an illustrative embodiment of the invention, the processor 404, memory 406, and/or clock functions 408 may be implemented using an Application Specific Integrated Circuit (ASIC), which allows controller 400 to be reduced in size in comparison to standard integrated circuit technology. However, it will be understood that the controller may be implemented using standard integrated circuit technology, or other technology, without departing from the scope of the present invention.

Processor function 404 executes instructions 402 used to control the functional components 410-490 of system 300. In particular, processor 404 executes instructions 402 necessary to perform the diagnostic test (e.g., as set forth in U.S. Pat. Nos. 6,743,635 and 6,946,299, incorporated by reference above). The instructions 402 for the processor 404 may be stored in memory 406 or elsewhere in the system. Memory function 406 may also store data, such as calibration data and other data, used in the performance of the diagnostic test as described, for example, in co-pending commonly-assigned U.S. patent application Ser. No. 11/144,715, filed Jun. 6, 2005, and incorporated herein by reference in its entirety. This memory may be in addition to, or the same as, the flash memory 148 of the data connector 602, as described above. In exemplary embodiments of the present invention, memory 406 is used to store results of the diagnostic test, which can include additional information such as time/date data and/or associated voice messages, for later processing.

Clock function 408 regulates the processor's execution of the instructions 402 in time. In particular, clock function 408 is used to regulate the timing of steps in the diagnostic test. For instance, processor 404 may use clock 408 to regulate an incubation time period, or other time periods, necessary for the correct performance of the diagnostic test (e.g., as set forth in U.S. Pat. Nos. 6,743,635 and 6,946,299, incorporated by reference above). Clock function 408 may be implemented by a single system clock or by multiple clocks for different purposes. Clock function 408 can be the same as, or in addition to, the clock function of crystal oscillator 138 of the data connector 602, as described above.

Media interface 410 accepts test media, such as test strips 120, for testing and can include a channel 411, or keyway, to ensure that the test media is correctly positioned when inserted by a user, or in an alternative embodiment, by the media dispensing mechanism 460. Interface 410 includes one or more media sensors for determining, e.g., whether a test strip 120 has been correctly inserted in the test port 410 (i.e., whether interface side 122 of test strip 120 is properly positioned with respect to the media sensors), whether an adequately-sized sample has been applied to the sample chamber on the sample side 121 of the test strip, and the presence or concentration of analyte in the sample. The interface can also detect strip coding information, as described in commonly-assigned co-pending U.S. patent application Ser. No. 11/181,778, filed Jul. 15, 2005, which is incorporated by reference herein in its entirety.

Power source 420 provides power to the electronic components of meter 130. In an illustrative embodiment, the power source is a lithium coin cell battery. However, other power sources, such as other types of batteries, solar cells, or AC/DC converters may be used without departing from the scope of the present invention. Power can be obtained through data connector 490, e.g., from a USB port of a computer to operate the meter when it is connected, or to recharge a battery. The output of the power source may be regulated, e.g., by a voltage regulator circuit.

User control function 430 may include, for example, one or more buttons, switches, keys or other controls for controlling the functions of meter 130. In an exemplary embodiment of the present invention, user control function 430 is implemented using a single control, e.g., a single button (not shown), that is used to control a plurality of meter functions. For example, user control 430 may be used to control the input/output function 440, indicator function 450, media dispensing mechanism 460, and/or voice message function 470, by providing commands to these functions directly or through controller 400. User control 430 may also be used to control the diagnostic test function of controller 400. For example, when a test is performed using a control solution (e.g., as set forth in U.S. Pat. Nos. 6,743,635 and 6,946,299, incorporated by reference above), the button (not shown) may be held down to indicate to controller 400 that the current sample is a control solution and, consequently, that controller 400 should perform a control test on the current strip.

Alternatively, a plurality of user controls, e.g., a plurality of buttons (not shown), may be provided, with each button having different functions. For example, two buttons may be provided to allow a user to scroll through diagnostic test results stored in the memory 406, in either forward or reverse directions. As an aid to the user, the function of the button or buttons at the particular time may be dynamically indicated by indicator function 450. For example, when reviewing previous test results, indicator function 450, e.g., a display 133 (as shown in FIG. 1), may instruct the user to "PRESS BUTTON TO VIEW NEXT RESULT." Further, user controls (not shown) may have different functions at different times. For example, holding a button (not shown) down upon the insertion of a test strip 120 into media interface 410 may command the controller 400 to perform a control test on that strip, whereas, holding the button down without inserting a test strip 120 may command the controller 400 to display the result of the previous diagnostic test.

The user control function can also be implemented by a partner device, such as a PC, MP3 player, cell phone, PDA, etc.

Input/output function 440 provides for the downloading of data or instructions 402 to meter 130, and/or the uploading of data from meter 130. Input/output function 440 may be used, for example, to upload the results of a diagnostic test or tests so that they may be transferred to a storage device, a flash memory 148, or a third party, via a network connection or wireless link, e.g., a healthcare professional. Alternatively, input/output function 440 may be used to download data (e.g., calibration data) or instructions 402 (e.g., updated software) to the meter 130, when appropriate. Input/output function 440 may be implemented using any conventional digital or analog information interface, e.g., a serial port, a parallel port, an optical port, an infrared interface, etc. The input/output function can also be implemented by a partner device, such as a PC, MP3 player, cell phone, PDA, etc. Networked partner devices could download and store updates for the meter 130, and install the updates the next time a connection with the meter 130 is achieved.

Indicator function 450 indicates the result of the diagnostic test to the user, e.g., as a numerical value together with the units of measurement. In addition to indicating the result of the diagnostic test, the indicator may present other information to the user. For example, the indicator 450 may indicate the average result of a plurality of tests, the time and/or date, remaining battery life, etc. (e.g., as set forth in U.S. Pat. Nos. 6,743,635 and 6,946,299, incorporated by reference above). Indicator 450 may also be used to prompt the user to perform certain steps of the diagnostic test, e.g., to apply the sample to the test strip 120. In an exemplary embodiment of the present invention (discussed below), indicator 450 indicates the number of test strips 120 remaining in container 110, the number of tests, or the time remaining before meter 130 becomes inoperative.

Indicator function 450 may present information in visible, audible or tactile form. For example, indicator 450 may include a display 133 for displaying information, e.g., using numerical values, words and/or icons. A number of different technologies may be used for display 133. For example, the display may be a liquid crystal display (LCD), a vacuum fluorescent display, an electroluminescent display, a LED display, a plasma display, etc. In an illustrative embodiment, display 133 is a LCD.

Alternatively or in addition, indicator 450 may include an audible indicator configured to indicate information by sound. For example, indicator 450 may include a speaker connected to a voice and/or sound circuit that is configured to, e.g., speak the result of the diagnostic test or to beep to indicate that an error has occurred. As a further alternative, indicator 450 may be implemented as a dynamic Braille indicator for use by the blind.

The indicator function can also be implemented by a partner device, such as a PC, MP3 player, cell phone, PDA, etc.

Figure 9:
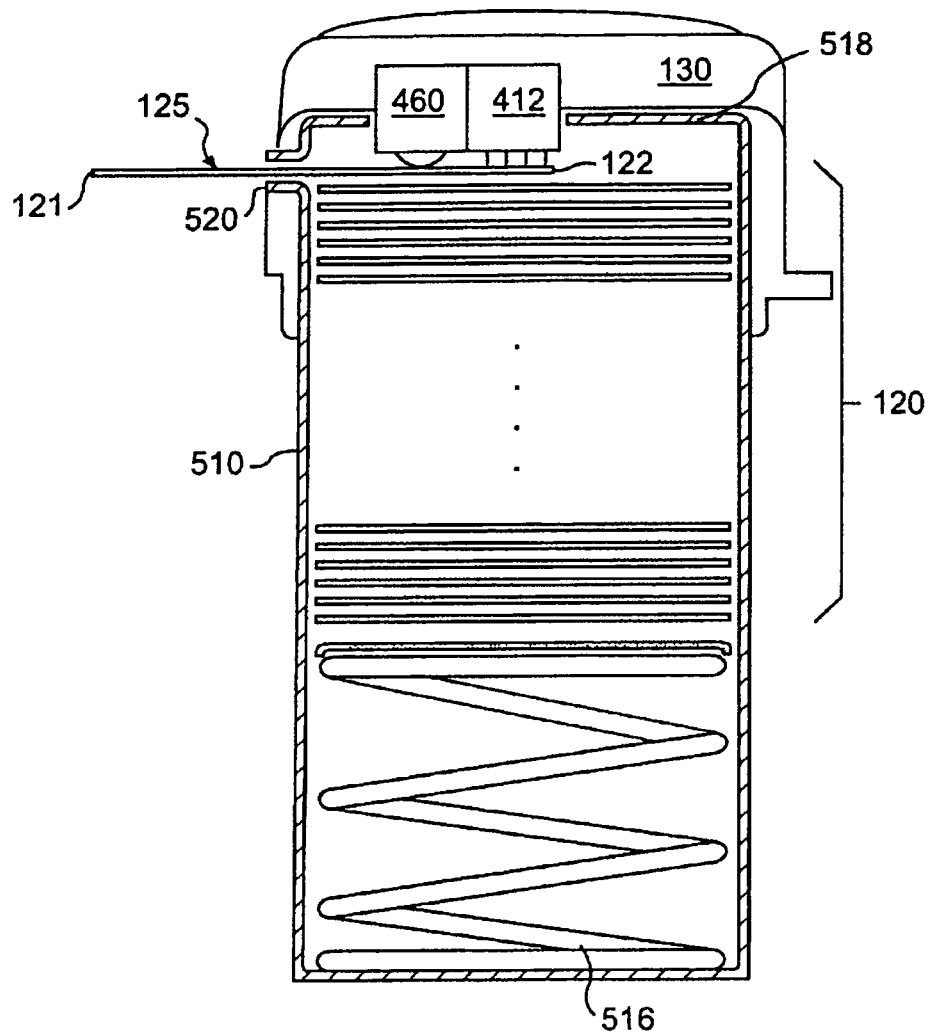
FIG. 9 is a cross-sectional view of a further illustrative embodiment of an integrated remote diagnostic system consistent with the present invention.

Because the diagnostic test media, e.g., test strips 120, is typically very small, certain users may find it difficult to retrieve the test media from the container 110. Accordingly, a media dispensing mechanism 460 may be used to provide automated dispensing of test media 120 from the container 110. FIG. 9 illustrates a cross-section of an exemplary diagnostic system having a media dispensing mechanism 460. In this embodiment, the container 110 is configured as a spring-loaded magazine 510. A plurality of test strips 120 are stacked on top of one another in magazine 510. Magazine 510 may have an interior shape similar to that of the test media in order to maintain the alignment of the stack. For example, for the test strip 120 depicted in FIG. 1, the interior of magazine 510 may be generally rectangular in cross-section.

Spring 516 pushes the stack of test strips against the top 518 of magazine 510, where the top test strip 125 is operably positioned with respect to strip dispensing mechanism 460. Dispensing mechanism 460 dispenses the top test strip 125 in the stack using a linear and/or rotational mechanical action. The mechanical action may be executed manually (e.g., by the user pulling a slide or rotating a wheel) or by a motor 412 (e.g., a stepper motor) actuated by user control function 430. The top test strip 125 is slid from the stack and through slot 520. The test media used with this embodiment may be modified by application of a non-friction coating or film, such as TEFLON, to one or both sides of slot 520 in order to ensure smooth ejection.

Where the particular diagnostic test requires that the test strip be inserted into the media interface 410 before the sample is applied, media dispensing mechanism 460 may position the interface side 122 of the ejected test strip 125 within media interface 410, e.g., with the interface side 122 of the test strip engaging the media sensors and the sample chamber 121 of the test strip. Alternatively, media dispensing mechanism 460 may simply present either end of the top test strip 125 to the user, who may then manually insert the test strip 125 into media interface 410 (either before or after the sample is applied, depending on the requirements of the particular diagnostic test). Controller 400 may be instructed to count the number of test strips 120 dispensed by media dispensing mechanism 460 and cause indicator function 450 to indicate, e.g., the number of test strips 120 remaining in magazine 510.

Although FIG. 9 depicts the meter 130 configured to form an integrated system with magazine 510, the media dispensing function can also be implemented by a partner device, such as a PC, MP3 player, cell phone, PDA, etc, or a separate device altogether.

Voice message function 470 may be used to record a voice message associated with a given diagnostic test result. When self-testing his/her blood glucose level, for example, a user may use voice message function 470 to record information related to their diet around the time of the diagnostic test. The voice message may be recorded in memory 406, along with a pointer associating it with a particular test result. The use of the voice message function 470 is more fully explained in prior application Ser. No. 10/764,974, entitled "MEDICAL DIAGNOSTIC TESTING DEVICE WITH VOICE MESSAGE CAPABILITY," filed Jan. 26, 2004, commonly assignee with the present application, and incorporated by reference herein in its entirety.

In a portable embodiment, at the end of the useful life of the meter 130, the meter may be given or sent to the user's medical care provider. The healthcare professional may then review the results of the diagnostic tests and/or associated voice messages for use in treating the user. The voice messages can also be downloaded with other data to a partner device. Additionally, the voice message function 470 can also be implemented by a partner device, such as a PC, MP3 player, cell phone, PDA, etc.

Environmental sensing function 480 may include one or more environmental sensors used to gather data used in the performance of the diagnostic test. Such environmental sensors may include, e.g., a temperature sensor and/or a humidity sensor. For example, meter 130 may use a temperature reading to correct the diagnostic test result for temperature dependence (e.g., as set forth in U.S. Pat. Nos. 6,743,635 and 6,946,299, incorporated by reference above). As a further example, meter 130 may use a humidity reading to determine if the humidity level is too high to proceed with the diagnostic test. Additionally, the environmental sensing function 480 can also be implemented by a partner device, such as a PC, MP3 player, cell phone, PDA, wireless weather station, internet weather service, etc.

4. Partner Device Electronics

Figure 10:
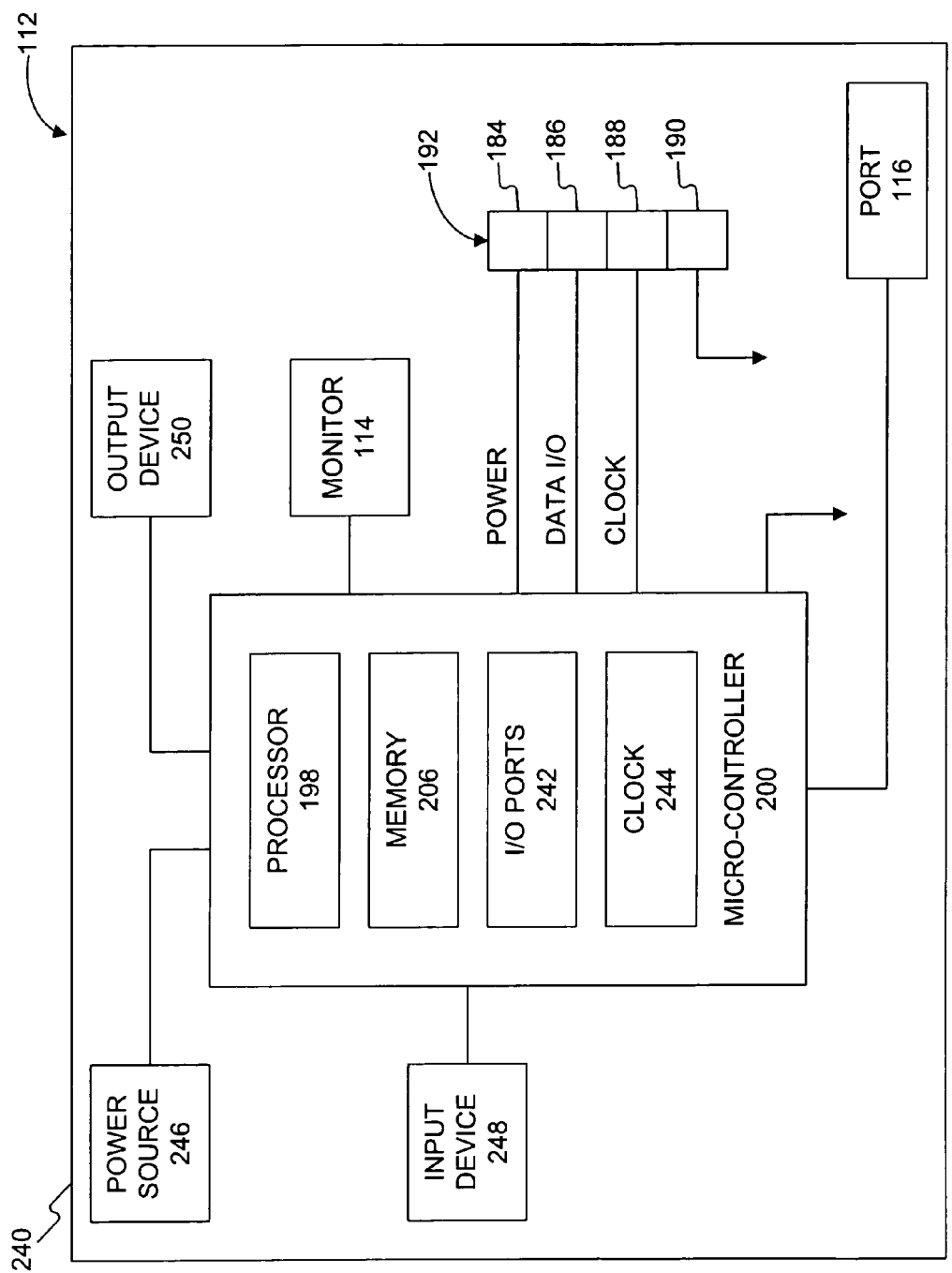
FIG. 10 is an exemplary block diagram of a prior art, general purpose computer usable with the present invention.

As described above, a partner device in the form of general-purpose computer 112 is further shown in FIG. 10. While discussed in terms of a general-purpose computer, it is to be understood that the partner device can take the form of many electronic devices, such as MP3 players, digital cameras, cell phones, PDAs, and combination and hybrid devices. These devices share many or all of the components discussed herein with reference to the general purpose computing system 112. FIG. 10 illustrates, in simplified form, a block diagram illustrating functional components of the computer 112. Computer 112 can include a power source 246, an input device 248, a microcontroller 200, an output device 250, a monitor 114, a data coupling 192, and a port 116. Possible input devices 248 include network interfaces, keyboards, mice, speech recognition devices, or document, video, or image input devices. Additionally, possible output devices 250 include network interfaces, printers, or sound or speech output devices. In an illustrative embodiment, the functional components of the computer 112 are contained within computer housing 240.

As further illustrated in FIG. 10, the computer system 112 can also include at least one microcontroller or central processing unit ("CPU") 200. CPU 200 can execute software programs for implementing some of the processes described below with respect to FIG. 11. Software programs for the computer system can reside in the memory 206 of the CPU 200. Memory 206 can include graphs, charts, etc., and software for manipulating the data.

Microcontroller 200 controls the operation of the functional components of the computer in accordance with its instructions, which can be provided as software or firmware. Microcontroller 200 can include a processor 198, memory 206, input/output ports 242, and clock functions 244. These functional components operate similarly to the functional components of controller 400 of meter 130, as described above.

5. Operational Aspects of the Diagnostic System

Illustrative methods for operating the above described systems are herein described, noting that the processes are discussed herein by way of example only. Various steps and sequences can be effected in practicing the invention, as would be evident to one of ordinary skill in the art.

Figure 11:
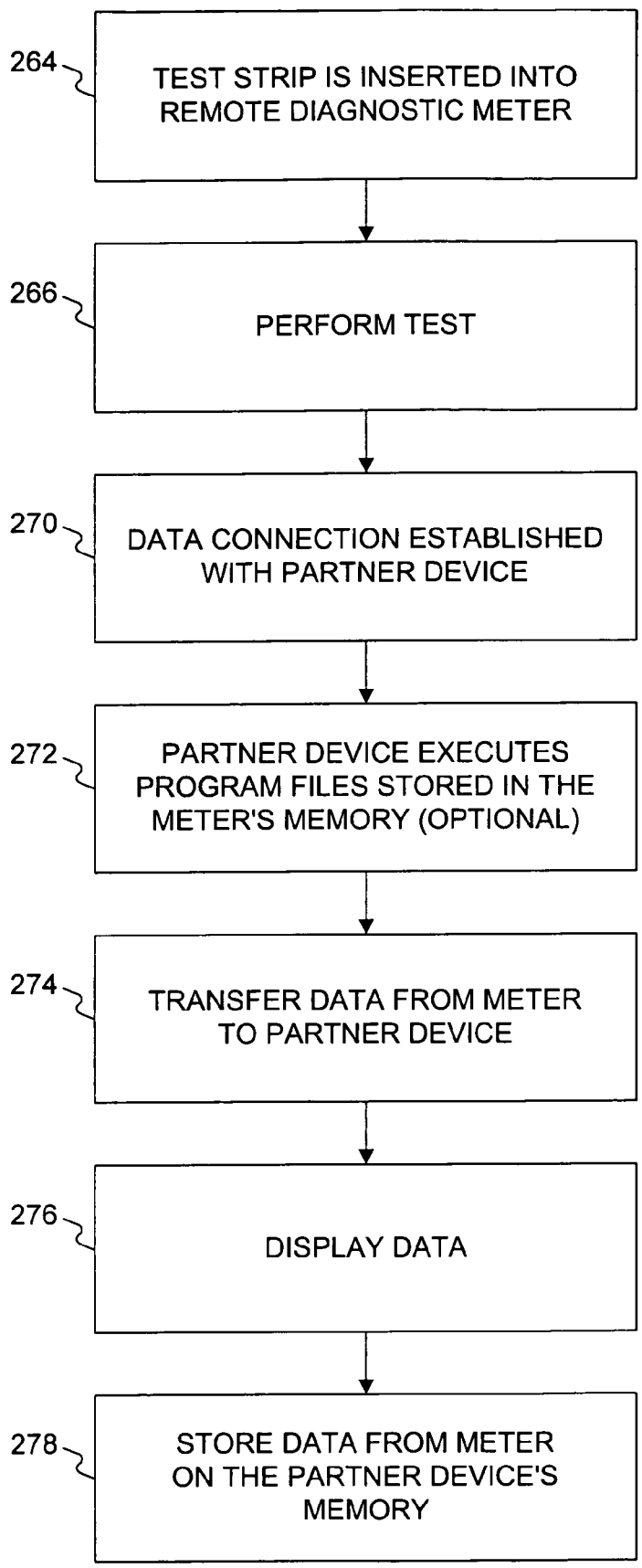
FIG. 11 is a flow chart illustrating a method of storing and auto-executing program files from a remote diagnostic meter to a personal computer.

As illustrated in the flowchart of FIG. 11, a user first inserts a test strip 120 into the diagnostic meter 130 in step 264. The meter 130 then performs an analytic test in step 266, and may display the results on a built-in display 133 of the meter 130. After the meter 130 performs one or more diagnostic tests, the data can be uploaded to a personal computer 112 for analysis, or transmitted to another party, such as a healthcare professional. In step 270, a data connection is established between the meter 130 and a partner device, such as a PC, PDA, MP3 player, cell phone, etc. This connection can be achieved via a USB connector, IEEE-1394 plug, wireless link, or other known connection methods, as described above. Of course, this data connection can be established before the diagnostic test is actually performed, which may be desirable, for instance, where the meter body is powered by the data connection, e.g. a USB connection. The partner device recognizes the interface, for example through Plug and Play protocols, and may optionally execute interface software contained resident in the memory of the meter 130, as illustrated in step 272. The desired test data is then transmitted from the meter 130 to the partner device as shown in step 274.

The test data can optionally be encrypted with device identification information, including the date and time the test result was obtained, a serial number of the meter, a user name, or other identifying data. Alternatively, the device and patient identification data can be transmitted from the meter together or sequentially, along with diagnostic test data, such that the computer software recognizes which data belongs with which user. The incoming data from the meter 130 can then be displayed on a partner device display and/or stored in a partner device memory to be accessed at a later time, as indicated by steps 276 and 278, respectively. Of course the partner device that displays the test results in step 276, and the partner device that stores the test results, need not ultimately be the same device. For example, the results from the diagnostic test may be displayed on a cell phone and subsequently stored on a hard drive of a PC.

Alternatively, the partner device can interface directly with the flash memory 148 of the meter's interface to transfer test data from the diagnostic meter 130 to the partner device.

Moreover, present and future-developed implementations of various plug and play protocols and standard driver libraries can allow other input/output device drivers to be used without floppy emulation, such as flash drive drivers, PDA drivers, or even digital camera and media player drivers, etc., and this configuration is explained herein by means of example.

6. Prevention of the Use of Incorrect Test Strips

As discussed above, diagnostic meter 130 may be calibrated for use with a particular lot of test media by coding with appropriate calibration parameters. In one method of preventing the use of incorrect test strips, the meter is configured to read a calibration code on the strip. The coding scheme can be similar to that described for on-strip coding in co-pending U.S. patent application Ser. No. 11/181,778, filed on Jul. 15, 2005, and commonly assigned with the present application, the contents of which are incorporated herein by reference. Another approach is to provide only strips corresponding to a preprogrammed set of calibration data for use with the meter. This approach is sometimes called "universal" coding.

Although the on-strip and universal coding methods described above are designed to prevent meter calibration errors, the diagnostic test system can further employ additional safeguards to minimize user error. For example, the integrated diagnostic system 100 can include one or more preventive measures that may disable one or more functions of the meter 130 upon the occurrence of certain triggering events. For instance, the triggering event can be a certain period of time elapsing, the performance of a predetermined quantity of tests, or with a certain quantity of test media. The meter 130 may then be simply disposed of or returned to the manufacturer for remanufacturing.

Alternatively, the preventive measure may render only the diagnostic testing function of controller 400 inoperative, or simply prevent the meter 130 from displaying the result of a diagnostic test. The user may then retain meter 130 in order to use its remaining functions. One having ordinary skill in the art will understand that many other safeguards may be employed to minimize and prevent meter calibration errors. After the meter is disabled, for example, the memory might still be accessed to download results. A disabled meter, in addition, might facilitate the automatic reordering of supplies through the partner device, e.g. an internet-enabled computer, or a cell phone.

The systems and methods disclosed herein can be embodied in various forms. Moreover, the above-noted features and other aspects and principles of the present invention can be implemented in various environments. Such environments and related applications can be specially constructed for performing the various processes and operations according to the invention, or they can include a general-purpose computer selectively activated or reconfigured by code to provide the necessary functionality. The processes disclosed herein are not inherently related to any particular computer or other apparatus, and can be implemented by a suitable combination of hardware, software, and/or firmware. For example, various general-purpose machines can be used with programs written in accordance with teachings of the invention, or it may be more convenient to construct a specialized apparatus or system to perform the required methods and techniques.

Additional benefits are possible through use of some aspects of the present invention. For instance, when the meter is connected to a partner device or network, software or firmware updates for the meter can be obtained and installed automatically from a manufacturer's web site, using, for instance, simple HTTP protocols.

Systems and methods consistent with the present invention also include computer readable media that include program instruction or code for performing various computer-implemented operations based on the methods and processes of the invention. The media and program instructions can be those specially designed and constructed for the purposes of the invention, or they can be of the kind well-known and available to those having skill in the computer software arts.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for diagnostic testing, the system comprising:
   a dual-functionality meter device configured to have two alternative modes of operation, wherein in a first mode the meter device performs a diagnostic test on a sample applied to test media, and in a second mode the meter device functions as a mass storage device, the meter device having a housing, the housing containing:
      a test media interface configured to receive test media for performing the diagnostic test, and
      a flash drive comprising a built-in USB data connector, a mass storage controller, a flash memory chip, and an oscillator chip.

2. The system for diagnostic testing of claim 1, wherein the meter housing further contains a display configured to display results of the diagnostic test.

3. The system for diagnostic testing of claim 1, wherein the meter housing is configured to be connected to a sampling device.

4. The system for diagnostic testing of claim 3, wherein the sampling device is a lancet.

5. The system for diagnostic testing of claim 1, wherein the meter housing is configured to be attached to a side portion of a test media container.

6. The system for diagnostic testing of claim 1, further comprising a data communication interface configured to establish data communication with a partner device.

7. The system for diagnostic testing of claim 6, wherein the partner device is selected from the group consisting of: a cell phone, a PDA, a general purpose computer, a digital media player, a digital camera, and wireless information device.

8. The system for diagnostic testing of claim 6, wherein a transceiver dock is hardwired to the partner device.

9. The system for diagnostic testing of claim 8, wherein the transceiver dock and the meter housing are wirelessly connected.

10. The system for diagnostic testing of claim 6, wherein a cradle is plugged into a socket of the meter housing to establish wireless data communication with the partner device.

11. The system for diagnostic testing of claim 10, wherein the cradle and the partner device are compatible with a wireless transmission protocol.

12. The system for diagnostic testing of claim 1, wherein the meter housing is configured to selectively close an opening of a test media container.

13. A diagnostic meter for performing a diagnostic test on a sample, the meter comprising:
    a test media interface configured to receive a test strip for performing the diagnostic test on the sample; and
    a flash drive comprising a built-in USB data connector, a mass storage controller, a flash memory chip, and an oscillator chip.

14. The diagnostic meter of claim 13, further comprising a display unit configured to display the result of the diagnostic test.

15. The diagnostic meter of claim 13, wherein the flash memory chip is further configured to store one or more communication protocol driver for interfacing with the partner device.

16. The diagnostic meter of claim 13, wherein the USB data connector is configured to establish data communication with a partner device, and further wherein the partner device comprises a data port adapted to interface with the USB data connector.

17. The diagnostic meter of claim 16, further comprising a rechargeable battery unit for providing power to the meter.

18. The diagnostic meter of claim 17, wherein the battery can be recharged by connecting the diagnostic meter to the partner device using the USB data connector.

19. The diagnostic meter of claim 13, wherein the flash memory chip is further configured to store instructions for processing the result of the diagnostic test.

20. The diagnostic meter of claim 16, wherein the partner device is selected from the group consisting of a computer, a PDA, a cell phone and a digital media player.

21. The diagnostic meter of claim 13, wherein the flash memory chip is a NAND-type flash memory device.

* * * * *